United States Patent [19]

Kajiura et al.

[11] Patent Number: 4,830,194
[45] Date of Patent: May 16, 1989

[54] GRANULE INSPECTION APPARATUS

[75] Inventors: Toshihiro Kajiura, Osaka; Norio Oita, Kobe; Junnosuke Abe, Osaka; Seiji Sugiyama, Kadoma, all of Japan

[73] Assignee: Kanebo Ltd., Tokyo, Japan

[21] Appl. No.: 89,302

[22] Filed: Aug. 25, 1987

[30] Foreign Application Priority Data

Nov. 6, 1986 [JP] Japan .................. 61-264837

[51] Int. Cl.⁴ .............................. B07C 5/342
[52] U.S. Cl. ....................... 209/580; 209/587; 209/588; 209/643
[58] Field of Search ............... 209/576, 577, 580, 587, 209/588, 639, 643, 644; 406/128, 131, 151, 152

[56] References Cited

U.S. PATENT DOCUMENTS

| | | | |
|---|---|---|---|
| 2,858,018 | 10/1958 | Alexander et al. | 209/644 |
| 3,685,650 | 8/1972 | Walther et al. | 209/581 |
| 3,738,485 | 6/1973 | Garland | 209/643 |
| 3,914,601 | 10/1975 | Hoover et al. | 209/587 |
| 4,147,619 | 4/1979 | Wassmer | 209/580 |
| 4,371,081 | 2/1983 | Satake | 209/580 |
| 4,373,638 | 2/1983 | Schapper | 209/587 |
| 4,699,274 | 10/1987 | Saika | 209/580 |

FOREIGN PATENT DOCUMENTS

159882 9/1983 Japan.
191944 8/1986 Japan.
210929 9/1986 Japan.

Primary Examiner—Johnny D. Cherry
Assistant Examiner—Donald T. Hajec
Attorney, Agent, or Firm—Stevens, Davis, Miller & Mosher

[57] ABSTRACT

A granule inspection apparatus comprising a pair of transparent rotating body installed in parallel at prescribed spacing, a granule falling passage being formed between mutually opposing surfaces of the rotating bodies, granules are fallen through this passage, falling granules are lighted by the reflection light source arranged on the side of one transparent rotating body and by the transmission light source arranged on the side of the other transparent rotating body, an image sensor is picked up the images of the lighted granules, presence of defectives is detected from image signals, a selector is driven to select non-defectives from defectives.

11 Claims, 11 Drawing Sheets

Granule : white
Background : black (A)

Entirely white surface (B)

Granule : black
Background : white (C)

Entirely black surface (D)

Entirely white surface (E)

Entirely white surface (F)

Foreign granule and
hair : black
Background : white (G)

Foreign granule and
hair : black
Background : white (H)

GRANULE INSPECTION APPARATUS

BACKGROUND OF THE INVENTION

The present invention relates to a granule inspection apparatus adapted to use in visual inspection of granules such as medicine (fine grain, granulated powder, and powder), electronic materials (ceramic powder), food (cereals, flour product such as bread crumbs) and selection and removal of defective and foreign matter.

Visual inspection and selection of granules of this type has been conventionally performed in a manner in which granules are placed in sheet form on a belt conveyor, visually inspected while being transferred, and defective granules and foreign matter is removed as it is found.

However, there were sufficient possibilities that differences in individual quality of inspectors, fatigue and other factors could have resulted in inconsistencies in accuracy of inspection, overlooked defective granules and foreign matter, and the reliability of inspection by such method was low. On the other hand, in order to improve the inspection accuracy, it is necessary to slow down the conveying speed of granules and spread them into sheet form as thin as possible, but such practice, if adopted, involved a problem that processing efficiency is caused to be extremely low.

Furthermore, because of the presence of human beings, there were also other problems that inspections must be carried out in an open environment while difficulties are involved in preventing attachment of dust to granules being inspected.

With an objective to solve such problems as above, a granule inspection apparatus is proposed in which an image pickup element is used to automatically conduct visual inspection of granules, selection and removal of defective granules and foreign matter, etc. For example, in Japanese unexamined patent publication No. 58-159882, an inspection device is disclosed wherein by means of a well-known lighting means used for a microscope etc. granules such as cereals are caused to fall spontaneously, these granules are lighted from one side as well as from opposite side, the quantity of reflected light and that of transmitted light are equalized, the image of granules is photographed from one side and processed to detect presence of defective granules and foreign matter whose lightness is different from that of nondefectives and thereby to select and remove such defective granules and foreign matter by means of an air gun etc.

However, because the granule inspection apparatus as described above was constituted such that granules simply fall spontaneously, it was difficult to form the thin falling layer of granules into a regular thickness and the inspection accuracy used to be unstable. There was further a problem that when a certain length of granules in sheet form had fallen, granules spread spontaneously causing the granule passage to become unstable, and in the case of fine particles, powder that flies up makes it difficult to select and remove defective and foreign matter so that such inspection apparatus cannot be put to use.

SUMMARY OF THE INVENTION

It is a main object of the present invention to provide a granule inspection apparatus which is capable of forming a thin falling layer of granules of regular thickness by which stable inspection accuracy is achieved.

Another object of the present invention is to provide a granule inspection apparatus which is capable of accomplishing selection and removal of defective granules and foreign matter with ease and certainty.

According to the present invention, a granule inspection apparatus is provided, which consists of a pair of transparent rotating bodies which rotate about a center axis thereof, a granule falling passage being formed between the mutually opposing parts of the rotating bodies by arranging the rotating bodies to be opposed in parallel with a predetermined spacing therebetween; a granule conveying means which positions an opening for falling granules at the upper part of the aforementioned granule falling passage and form granules into sheets to be conveyed; a selector which is installed at the lower part of the granule falling passage to remove granules; a cleaner which cleans the mutually opposing surfaces of the pair of transparent rotating bodies respectively at positions other than the granule falling passage; a light source for reflection which lights granules, that are falling through the aforementioned granule falling passage, from the side of one transparent rotating body; a light source for transmission which lights granules, that are falling through the aforementioned granule falling passage, from the side of the other transparent rotating body; an image sensor which picks up images of granules falling through the granule falling passage from the side of the aforementioned one transparent rotating body; an image processing means which processes image signals of the image sensor to detect the presence of defective granules and foreign matter, etc. in granules falling down through the granule falling passage and issues defective warning signals; a selector controlling means which causes granules containing defective granules and foreign matter to be removed by the selector to operate for a prescribed period of time in response to defective warning signals from the image processing means; and the quantity of the light of the aforementioned light source for reflection which is reflected from non-defective granules being equalized to the quantity of the transmitted light from the aforementioned light source for transmission.

As described above, granules are caused to fall down through the granule falling passage which is formed by installing a pair of transparent rotating body at a certain spacing. Therefore, it becomes possible to easily form the granule falling layer of regular thickness and to stabilize the inspection accuracy. Further, because the diffusion (scattering, flying about, etc.) of granules is controlled by the granule falling passage, selection and removal of defective granules and foreign matter can be easily and positively accomplished. Also, because the transparent rotating body is cleaned by the cleaner, inspection will not become impossible by granules attaching to the transparent rotating body.

The above and other objects, features and advantages of the present invention will become more apparent from the following description when taken in conjunction with the accompanying drawings in which preferred embodiments of the present invention are shown by way of illustrative example.

BRIEF DESCRIPTION OF THE DRAWINGS

FIGS. 15(A) to 15(H) are schematic diagrams showing an image in an effective area of a TV image;

DETAILED DESCRIPTION

An embodiment according to the present invention will be described with reference to FIG. 1 to FIG. 12.

Figure 1:
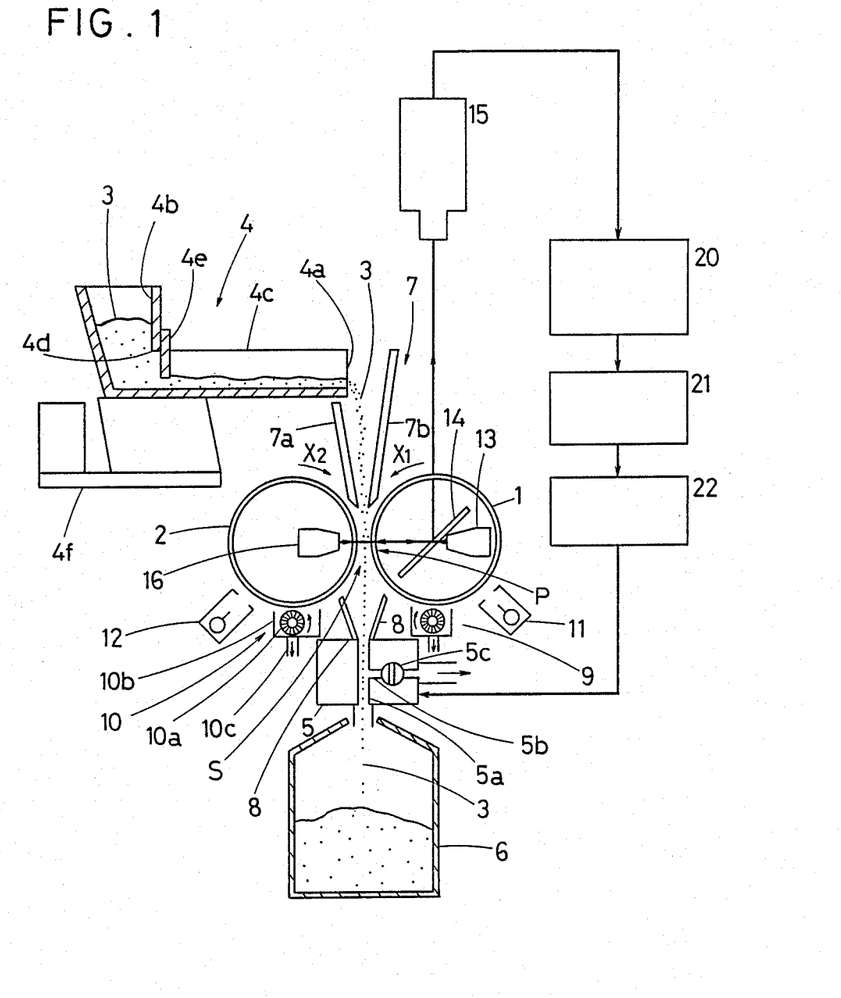
FIG. 1 is a schematic diagram of the granule inspection apparatus of an embodiment according to the present invention.

As shown in FIG. 1, this granule inspection apparatus comprises the following arrangements wherein two transparent rotating cylinders 1, 2 (made from glass and plastics, etc.) rotate about their respective center axes which are mounted horizontal and form the granule falling passage S by installing these two cylinders 1, 2 to be opposed with a predetermined spacing therebetween; an opening 4a for falling granules at the vibrating feeder (a granule loading and conveying means) is positioned at the upper part of the granule falling passage S; the selector 5 of the removal system (by means of air suction or discharge) is installed at the lower part of the granule falling passage S and the non-defective granules recovery container 6 is installed under the selector 5; the falling guide 7 made from transparent glass for example (the glass need not be transparent but material other than glass may be used) is arranged between the opening 4a of the vibrating feeder 4 and the upper end of the granule falling passage S formed by the two transparent rotating cylinders 1, 2; and the recovery guide 8, which may be made as one-piece with the selector 5, is disposed of between the lower end of the granule falling passage S and the selector 5.

The vibrating feeder 4 is made by joining the vibrating through 4 at the lower opening 4d of the granule storage bin 4b and has a partition board 4e for conveying quantity adjustment installed vertically movable at the lower opening of the granule storage bin 4b. By vibrating the whole construction by means of the vibrator 4, granules 3 are conveyed in sheet form in a fixed quantity and cause to fall granules 3 from the opening 4a. As compared with other conveying means, the vibrating feeder 4 has good quantifying capability and less clogging, is capable of closed operation and of easy cleaning (at the time of a large change or of a part change) of granule passing route, can be built at low cost, and therefore is optimum conveying means of the granules 3.

Figure 2:
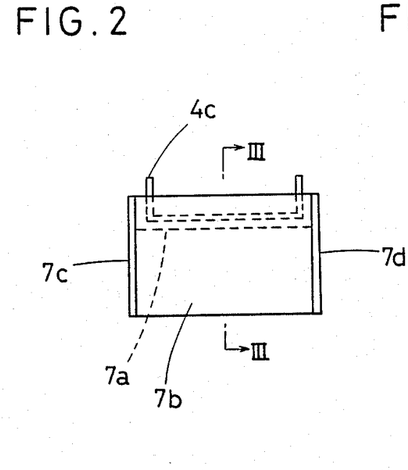
FIG. 2 is a front view showing the vicinity of the falling guide.
Figure 3:
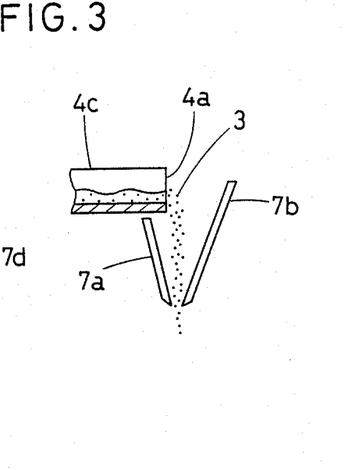
FIG. 3 is a cross sectional view along the line III—III shown in FIG. 2.

The falling guide 7 comprises, as shown in FIGS. 2 and 3, the following arrangements wherein two transparent boards 7a, 7b are disposed of in V configuration, side boards 7a, 7b are installed on both sides of the boards 7a, 7b to form a wedge shape, thereby controlling the diffusion (scattering) of granules 3 falling from the opening 4a of the vibrating feeder 4 so as to guide granules 3 into the granule falling passage S.

Figure 4:
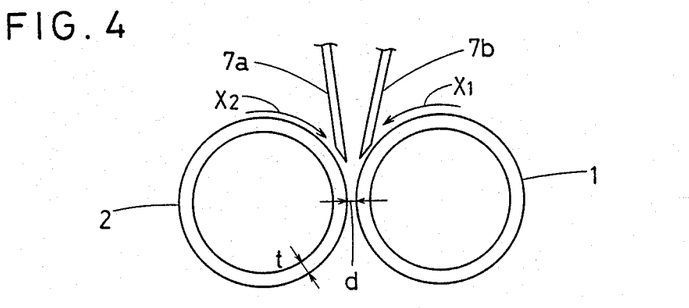
FIG. 4 is a side view showing the transparent rotating cylinder.

As shown in FIG. 4, the two transparent rotating cylinders 1, 2 are arranged as follows: The thickness t of these cylinders 1, 2 is several mm respectively and the space d between the mutually opposing surfaces is made to be several mm, the rotating direction is downward at mutually opposing angles as shown by arrow marks $X_1$, $X_2$ (i.e., the same direction as the falling direction of granules 3), so that the falling of granules 3 is not influenced.

The selector 5 shown in FIG. 1 comprises the following arrangement wherein the selector 5 comprises granule falling passage 5a and the removal passage 5b crossing to form the letter of T with this granule falling passage 5a so that granules 3 are removed by performing air suction from the removal passage 5b. Normally, the valve 5c provided in the removal passage 5b is closed and suction and removal operations are not performed, but when defective granules or foreign matter are contained in granules 3, the valve 5c is opened to suck and remove granules 3 by the selection signal sent from the processing circuit to be referred later.

Granules 3 are smoothed off into thin sheets by the vibrating feeder 4 to be conveyed in a fixed quantity, are introduced into the granule falling passage S by controlling the granules 3 to prevent scattering and diffusing by means of the falling guide 7 causing the granules 3 to fall through the granule falling passage S, and granules 3 are inspected while they are passing through the granule falling passage S. Granules 3 coming out of the granule falling passage S are guided into the selector 5 by means of the recovery guide 8 (to prevent scattering and diffusing), and if defective granules and foreign matter is included in granules are found out by the above inspection, granules 3 in the area containing defective granules and foreign matter are sucked and removed, non-defective granules are caused to pass the selector 5 as they are so as to be accumulated in the non-defective granule recovery container 6 installed under the selector 5.

As described above, by arranging two transparent rotating cylinders 1, 2, the granule falling passage S of small thickness is formed to allow granules 3 to pass through this granule falling passage S so that the granules 3 are inspected while they pass through the passage S. Therefore, the positional accuracy during inspection of falling granules 3 is good, and further the inspection accuracy can be improved because the granules 3 can be formed into a thin layer. Further, by means of the falling guide 7 which guides granules 3 up to the upper end of the granule falling passage S from the opening 4a of the vibrating feeder 4, scattering and flying about etc. of granules 3 prior to inspection can be prevented.

Furthermore, because granules 3 are guided by the recovery guide 8 from the lower end of the granule falling passage S to the selector 5, it is possible to send granules 3 into the selector 5 reliably and granules 3 are not allowed to scatter nor fly about, so that removal by the selector 5 of granules 3 in an area containing defective granules and foreign matter can be easily and reliably accomplished.

In order to prevent contamination of the outer surface of the two transparent rotating cylinders 1, 2 caused by granules 3 attaching thereto, as shown in FIG. 1, the cleaners 9, 10 and the static eliminators 11, 12 are provided at positions other than the granule falling passage S.

The cleaner 10 comprises rotating brush 10a which is driven by a motor etc. to brush off granules 3 attaching to outer surface of the transparent rotating cylinders 2, the housing 10b which envelopes the rotating brush 10a, and the air suction part 10c which sucks and removes granules 3 brushed off into this housing 10b. The cleaner 9 has the same construction as that of the cleaner 10.

The static eliminators 11, 12 remove the static electricity charged over outer surface of the transparent rotating cylinders 1, 2 by means of, for example, a corona discharging system to prevent granules 3 from attaching to the outer surface of the transparent rotating cylinders 1,2.

In a manner as stated above, granules 3 attached to the transparent rotating cylinders 1, 2 are always cleaned and removed by the cleaners 9, 10 and the static electricity charged on the outer circumference of the transparent rotating cylinders 1, 2 is removed by means of the static eliminators 11, 12 thereby to prevent granules 3 from attaching to the transparent rotating cylinders 1, 2 due to static electricity.

Therefore, the inspection cannot become impossible due to granules 3 which attach to the outer surface of the transparent rotating cylinders 1, 2. Furthermore, because the inspection cannot be prevented by cleaning of granules and removal of static electricity, high inspection efficiency can be achieved.

The method of inspection of granules 3 will be described as follows: Inside of one transparent rotating cylinder 1 is arranged the light source for reflector 13 to irradiate a light against the inspection area P through the half mirror 14, and the light reflected by granules 3 positioned in the inspection area P is further reflected by the half mirror 14 thereby to be caused to enter into the upper first dimensional image sensor 15. On the other hand, a transmission light 16 is arranged inside the other transparent rotating cylinder 2 to irradiate the light against the inspection area P, and the light passing through the clearance of falling granules 3 is reflected upward by the half mirror 14 to further reflect the light against the first dimensional image sensor 15 disposed above the half mirror 14.

The area including the inspection area P formed in line is picked up by the first dimensional image sensor 15 at every prescribed time, so that the presence of defective granules and foreign matter is judged based on image signals coming from the first dimensional image sensor 15.

In the above case, the quantity of the light of the light source for reflection 13 reflected by non-defective granules and the quantity of the light of the light source for transmission 16 transmitted from the transparent rotating cylinder 2 are set in an equal amount. More specifically, the quantity of these lights are established by the transmission factor of the transparent rotating cylinder 2 and adjustment of light quantity of the light source for transmission 16.

Figure 5:
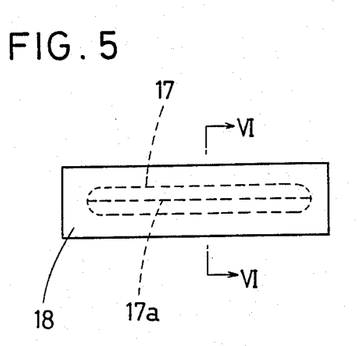
FIG. 5 is a front view showing the light source for transmission.
Figure 6:
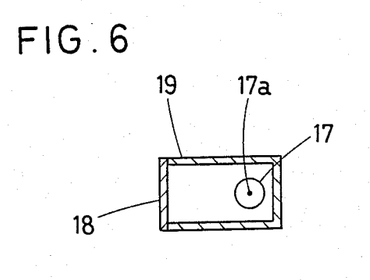
FIG. 6 is a cross sectional view along the line VI—VI shown in FIG. 5.
Figure 7:
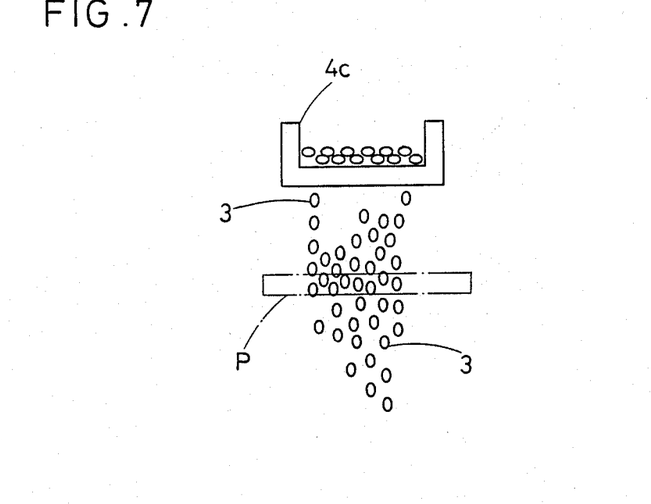
FIG. 7 is a schematic diagram showing the inspection area.

It should be noted that the light source for transmission 16, as shown in FIG. 5 and FIG. 6, comprises the case 19 which accommodates the linear light source lamp 17 (multiple light source may be used) having a linear filament 17a disposed of along the tube axis inside a cylindrical glass tube and the diffusion panel 18 fitted on the front opening of the case 19, the tube axis of the linear light source lamp 17 is arranged in the transparent rotating cylinder 2 so that the tube axis of the lamp 17 is parallel with the center axis of the transparent rotating cylinder 2 thereby permitting the light emitted from the diffusion panel 18 to transmit and light the inspection area P.

The light source for reflection 13 has the same structure as that of the light source for transmission 16.

When a granule inspection apparatus is constituted in a manner as described above, if all the granules 3 which are falling are non-defective granules, the image picked up by the first dimensional image sensor 15 will have the same lightness over an entirety of the inspection area P and the granules 3 become invisible completely. If, however, defective granules and foreign matter are mixed in granules 3, such objects differ in reflected light quantity from that of non-defective granules, that is, the lightness of such objects is different from that of non-defective granules, and an image of the first dimensional image sensor 15 under such condition will have dark parts and bright parts produced corresponding to defective granules and foreign matters. Consequently, the presence of dark spots or bright spots in an image are detected by the image processor 20 which will be described in detail. If any dark spots or bright spots are present, the selector 5 is caused to operated for a prescribed period of time by the selector controlling means (21, 22) so that granules 3 in an area where defective granules and foreign matters are sucked and removed.

The resolution of inspection will hereafter be described.

A first dimensional image sensor 15 with resolutions of 1000 dots and 2000 dots is available and such image sensor with resolution of 5000 dots/line is also sold, enabling inspection (inspection of quantity processing) of high accuracy or wide range. In continuous inspection, the first dimensional image sensor 15 is advantageous and the resolution in the width direction is determined by the magnifying power of the camera lens system. In an embodiment according to the present invention, the magnifying power is set to 50 microns per senser dot.

The vibrating feeder 4 can convey granules 3 stably despite generally slow linear speed of conveyance and even if a thick layer is caused to fall from the opening 4a to improve the inspection speed, the gravity acceleration g during falling and the probability of falling thick layer smooth off granules 3. Therefore, layer of granules in the inspection area P becomes fairly thin and there is least probability that defective granules and foreign matters are hidden behind the shadow of non-defective granules thereby making inspection impossible (See FIG. 7).

The image processor 20 which generates defective warning signals based on the image of the first dimensional image sensor 15 and the selector controlling means (21, 22) will hereafter be described in detail with reference to FIG. 8 to FIG. 12.

Figure 8:
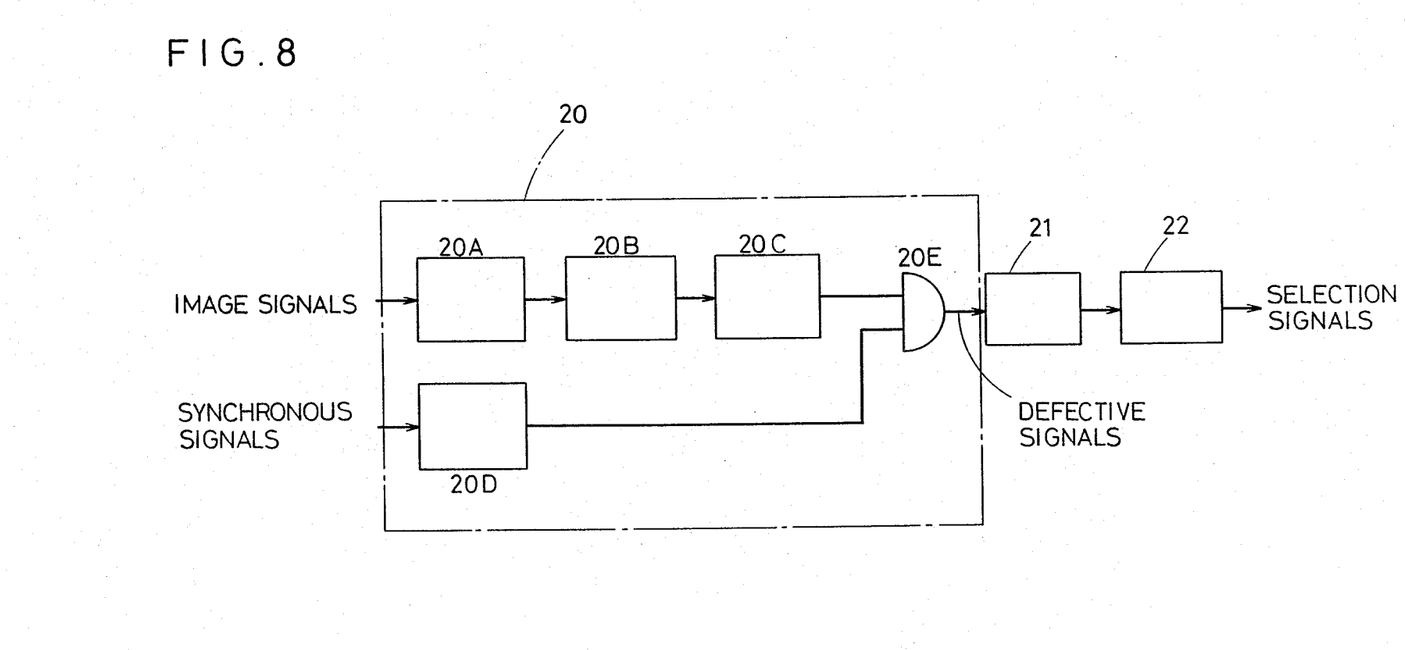
FIG. 8 is a block diagram showing details of the electric circuit shown in FIG. 1.

The image processor 20 which processes image signals from the first dimensional image sensor 15 amplifies image signals and removes noise by passing image signals through the amplifying filter circuit 20A as shown in FIG. 8. By further passing image signals through the differentation circuit 20B, characteristic signals corresponding to singular points in images are obtained, and these characteristic signals are descriminated of its levels by positive and negative differential level comparator 20C. On the other hand, based on the synchronous signals, mask signals which control the inspection area P are generated from the mask signal generating circuit 20D and by controlling the AND gate 20E with these mask signals defective signals are issued when dark points or bright points are present in the effective area (corresponds to the inspection area P).

Figure 9:
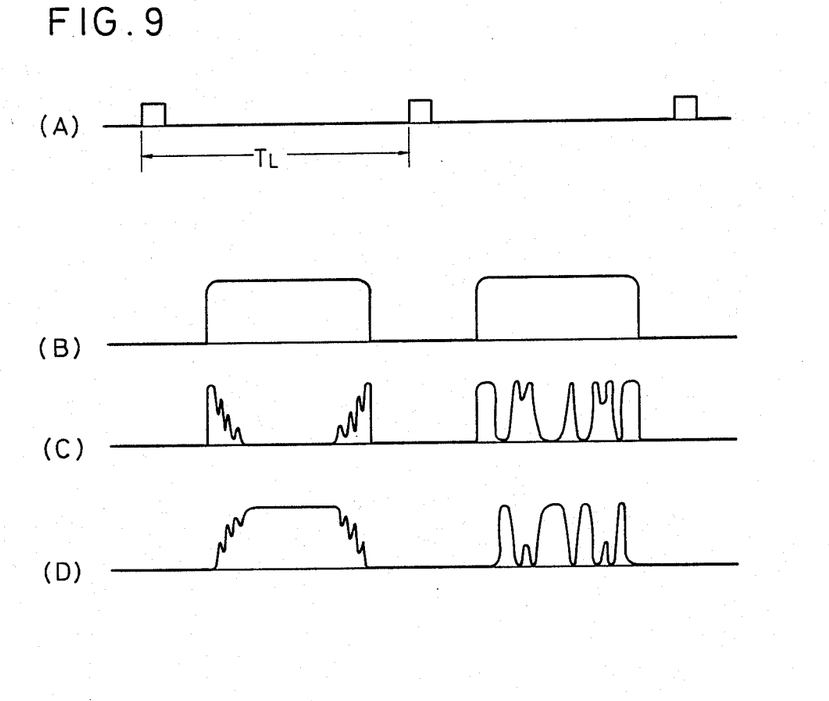
FIG. 9 is a signal waveform diagram showing components of the line sensor camera.

FIG. 9 shows signal waveforms of the first dimensional image sensor 15, wherein (A) is the line scan signal and $T_L$ is the line scanning rate. (B) is the picture signal of the first dimensional image sensor 15 when the reflected light quantity and the transmitted light quantity are balanced, and the first half represents the case wherein granules 3 cover the whole of the inspection area P while the latter half represents the case wherein granules 3 are dispersed in the inspection area P.

(C) is the picture signal of the first dimensional image sensor 15 when only the lighting by the transmission light source 16 is used, and the first half represents the case wherein granules 3 cover the whole of the inspection area P while the latter half is the case wherein granules 3 are dispersed in the inspection area P.

(D) is the picture signal of the first dimensional image sensor apparatus 15 when only the lighting by the reflection light source 13 is used, and the first half represents the case wherein granules 3 cover the whole of the inspection area P while the latter half represents the case wherein granules 3 are dispersed in the inspection area P.

Operations of the circuits shown in FIG. 8 will now be described in detail by way of FIG. 10 to FIG. 12. When defective granules and foreign matters do not exist but only non-defective granules are present in the inspection area P, the picture signal of the first dimensional image sensor 15 becomes a flat and almost trapezoidal waveform as shown in FIG. 10 (A).

Figure 10:
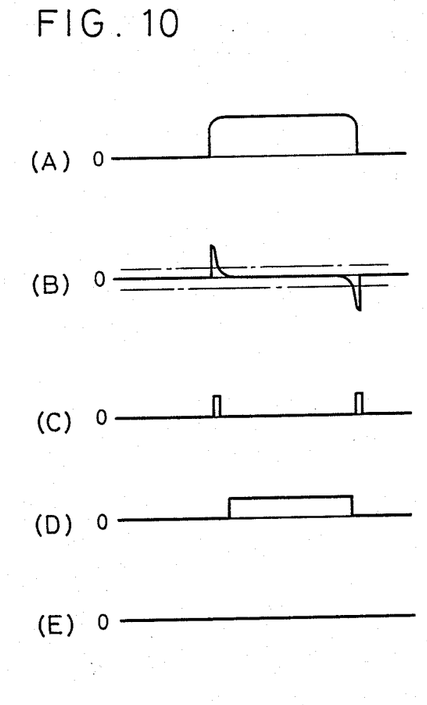
FIGS. 10, 11, and 12 are signal waveform diagrams showing components shown in FIG. 8.

The differential signal obtained by differentiating this picture signal produces pulses corresponding to the leading edge and the trailing edge of the picture signal as signal as shown in FIG. 10 (B) while the output of the positive and negative differential level comparator 20C produces pulses corresponding to the leading edge and the trailing edge of the picture signal as shown in FIG. 10 (C). However, because these pulses are outside of the on-period of the mask signals shown in FIG. 10 (D), the defective signal from AND gate 20E remains as L level as shown in FIG. 10 (E).

Figure 11:
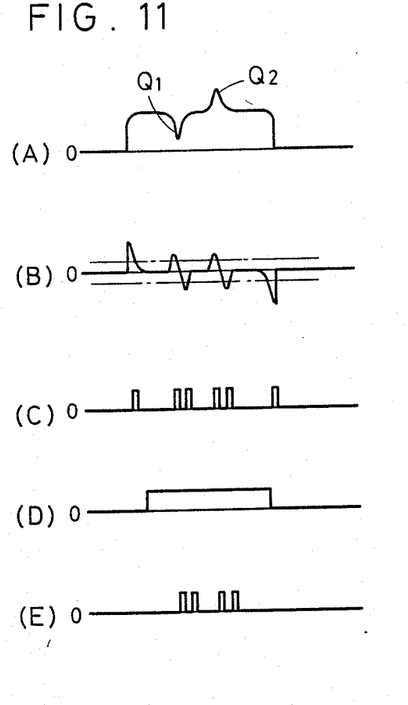

On the other hand, when defective granules and foreign matter exist in the inspection area P, the picture signal of the first dimensional image sensor 15 becomes a waveform having recess (black one) and height (bright one) in response to the presence of foreign matter etc. as shown in FIG. 11 (A).

The differential signal obtained by differentiating this picture signal produces pulses corresponding to the leading edge and the trailing edge as well as the recess $Q_1$ and the height $Q_2$ of the picture signal as shown in FIG. 11 (B) while the output of the positive and negative level comparator 20C produces pulses (H level) corresponding to the leading edge and the trailing edge as well as the recess $Q_1$ and the height $Q_2$ of the picture signal as shown in FIG. 11 (C).

However, because the pulses corresponding to the leading edge and the trailing edge of the picture signal are outside of the on-period of the mask signals as in the aforementioned case, the defective signal from AND gate 20E will not be the H level as shown in FIG. 11 (E), but, because the pulses corresponding to the recess $Q_1$ and the height $Q_2$ of the picture signal are inside of the on-period of the mask signals, the defective signal from AND gate 20E becomes H level as shown in FIG. 11 (E).

Figure 12:
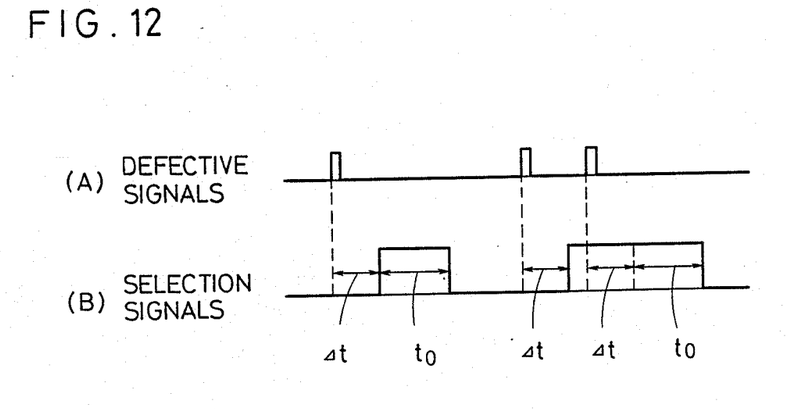

In this way, the defective signal (of H level) shown in FIG. 12 (A) being output from this AND gate 20E is added to retriggerable one-shot multiple vibrator 22 through the delay circuit 21 and the selector 5 actuates during output pulse generating period of this retriggerable one-shot multiple vibrator 22 so as to suck and remove granules 3.

The delay circuit 21 of above delays the defective signal by $\Delta t$ time and adds the delayed time to the retriggerable one-shot multiple vibrator 22. The delay circuit 21 further determines the delay time $\Delta t$ considering the time of defective granules and foreign matter reaching the removal passage 5b of the selector 5 and the delay in operation of the selector 5 after defective granules and foreign matter are located in the inspection area P and defective warning signals have generated, thereby to lessen the loss of non-defective granules of granules 3.

The retriggerable one-shot multiple vibrator 22 outputs pulses for $t_0$ time after entering defective signal which is set to a time necessary to suck and remove defective granules and foreign matters.

The retriggerable one-shot multiple vibrator 22 outputs pulses as selection signals as shown in FIG. 12 (B) against the defective signals shown in FIG. 12 (A).

According to this embodiment of the present invention, by employing the transparent rotating cylinders 1,2, adjustment of the reflected light quantity and the transmitted light quantity can be easily made (by adjusting the transmission factor of the transparent rotating cylinders 1,2) and optical extraction of defective granules for example is facilitated.

Because the reflection light source 13, the transmission light source 16, and the half mirror 14 are arranged inside the transparent rotating cylinder, downsizing of the apparatus can be achieved.

The transmission light source 16, the reflection light source 13, and the half mirror 14 may be disposed of outside the transparent rotating cylinders 1,2.

Further, it is preferred that the granule passing route is covered as much as possible, granules 3 (fine powder) flying about from gaps of parts of the vibrating feeder 4 and the transparent rotating cylinders 1, 2 are removed by the suction nozzle, and suction nozzles are installed at parts of such vibrating feeder and rotating cylinders thereby to prevent scattering of granules 3 to equipment (first dimensional image sensor 15, reflection light source 13, transmission light source 16, half mirror 14, and inside of transparent rotating cylinders 1, 2, etc.).

The transparent rotating cylinders 1, 2 may be installed in parallel with the center axis being vertically so as to cause granules to fall between the cylinders, but it is preferred to arrange the center axis horizontally in view of the inspection accuracy and the inspection speed.

Figure 13:
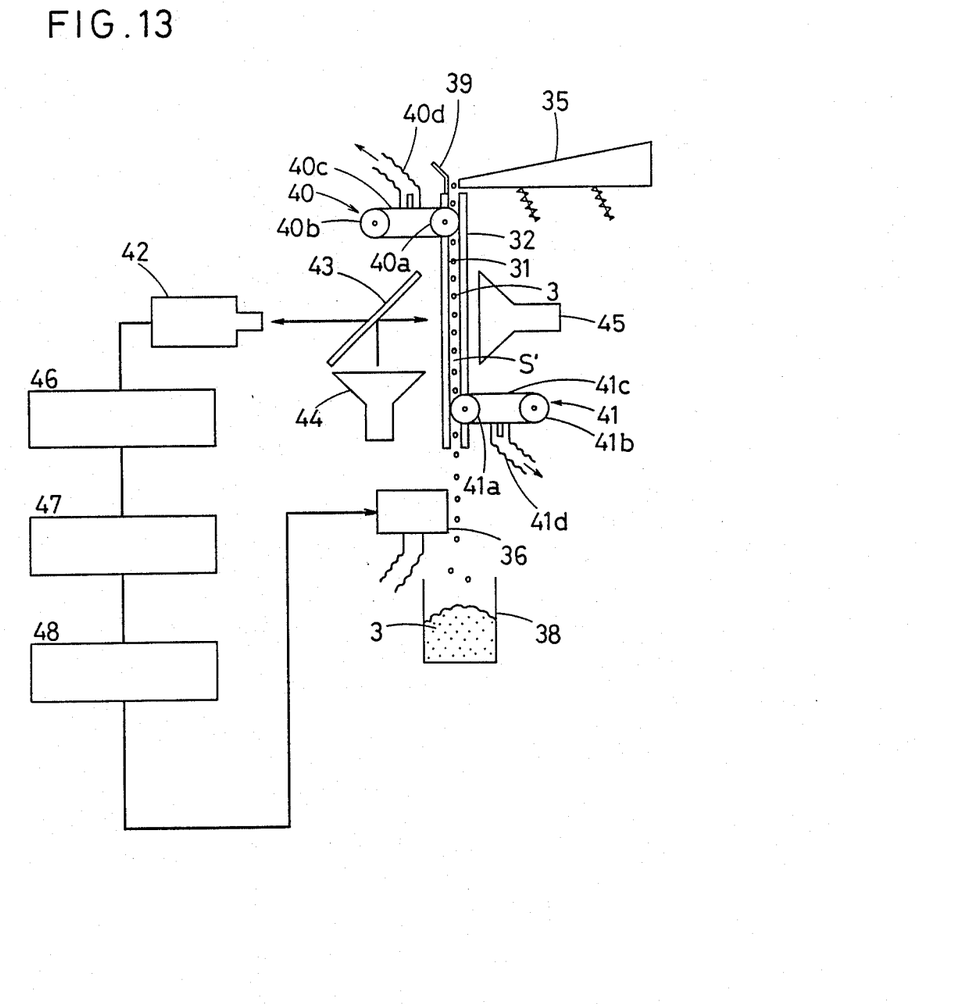
FIGS. 13 and 14 are schematic diagrams respectively showing other embodiments according to the present invention.
Figure 14:
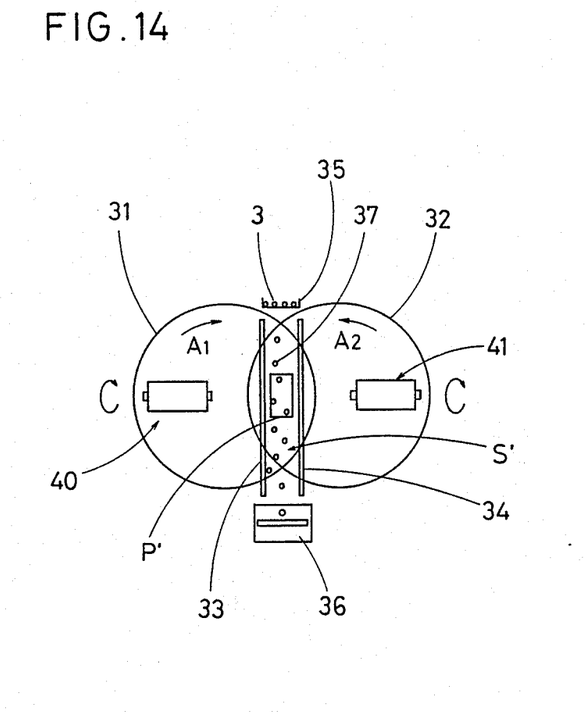

Other embodiments according to the present invention will be described based on FIG. 13 to FIG. 15. As shown in FIG. 13 and FIG. 14, this granule inspection apparatus has the following arrangements, wherein two pieces of transparent glass disks (may be made from plastic material) 31, 32 are installed in parallel to oppose each other in part at prescribed spacing; by installing two guide side boards 33, 34 in parallel at a prescribed spacing between mutually opposing surfaces of the aforementioned two pieces of glass disks 31, 32, the granule falling passage S' is made for granules to be inspected, the opening for falling granules of the granule loading and conveying means such as the vibrating feeder 35 is positioned at the upper end of the granule falling passage S' and the selector 36 is installed under the granule falling passage S'; granules 3 are smoothed into thin sheets to be conveyed by the vibrating feeder 35 so as to causing granules 3 to fall while granules 3 are controlled of diffusion through the granule falling passage S'; granules 3 are inspected as they are passed through the granule falling passage S' and if defective granules and foreign matter are included, the selector 36 is actuated to remove granules 3 in the area containing defective granules and foreign matter; and non-defective granules are accumulated in the nondefective recovery container 38 arranged directly below the granule falling passage S'.

In FIG. 13, a guide 39 is provided for introducing granules 3 into the granule falling passage S'.

Thus, the granule falling passage S' of small thickness is made using two pieces of glass disks 31, 32 and two guide side boards 33, 34 and granules 3 are caused to pass through this granule falling passage S'. Accordingly, positioning accuracy of falling granules 3 is good, and also because granules 3 can be made into thin layer, the inspection accuracy can be improved.

Further, because granules 3 do not diffuse, removal of granules 3 in the area containing defective granules and foreign matter detected by the selector 36 can be made with ease and certainty.

Furthermore, the aforementioned two pieces of glass disks 31, 32 rotate at a constant speed (driven by a motor) in opposite directions (arrows $A_1$, $A_2$) about the center axis as the rotating axis, so that the mutually opposing surfaces are cleaned by the cleaners 40, 41 at a position other than the granule falling passage S'.

These cleaners 40, 41 consist of the two drums 40a, 40b, 41a, 41b which are arranged in parallel respectively, looped cleaner cloth 40c, 41c which envelope these drums 40a, 40b, 41a, 41b, and the air suction sections 40d, 41d which suck and remove granules 3 attaching to the cleaner cloth 40c, 41c; one of the drums 40a, 41a is placed in contact with the surfaces of the glass disks 31, 32 where granules are attached by means of the cleaner cloth 40c, 41c; by rotating the drums 40a, 40b, 41a, 41b the surfaces of the glass disks 31,32 are cleaned with the cleaner cloth 40c, 41c; granules 3 attached to the cleaner cloth 40c, 41c are removed by means of the air suction sections 40d, 41d; and the surface of the glass disks 31,32 are cleaned with the cleaner cloth 40c, 41c.

As described above, since granules 3 attached to the glass disks 31, 32 are always removed by the cleaners 40, 41, inspection cannot become impossible by granules 3 which are attached to the glass disks 31, 32 while granules are falling. Moreover, there is no possibility for the inspection to be hindered by cleaning but the inspection effeciency is enhanced.

The following describes how to inspect granules 3.

The two dimensional image sensor 42 (TV camera, image sensor etc.) is installed in front of the mutually opposed surfaces of the two glass disks 31, 32 so that the area (refer to FIG. 14) including the inspection visual field P' established on the mutually opposing surfaces of the two glass disks 31, 32 is picked up at every prescribed time by means of the two dimensional image sensor 42; the half mirror 43 is arranged between the two dimensional image sensor 42 and the glass disks 31, 32; light is irradiated by the reflection light source 44 against falling granules 3 from the front of the glass disks 31, 32; the reflected light from granules 3 is caused to go into the two dimensional image sensor 42 by means of the half mirror 43; light is irradiated toward falling granules 3 by the transmission light source 45 from the rear position of the glass disks 31, 32; and the light transmitted through the gap between the glass disks 31, 32 and granules 3 is caused to enter further into the two dimensional image sensor 42 through the half mirror 43.

In this case, too, as in the aforementioned embodiment, the reflected light quantity of non-defective granules from the reflection light source 44 and the transmitted light quantity of the glass disk 32 from the transmission light source 45 are set in equal amount.

Accordingly, if falling granules 3 are all non-defective, the image photographed by the two dimensional image sensor 42 will have the same lightness in the entire area of the inspection visual field P' and granules 3 becomes invisible completely.

However, if defective and foreign matter are mixed in granules 3, reflected light quantity of the defective granules and foreign matter is different from that of non-defectives, that is, the lightness differs between the defective granules or foreign matter and the non-defectives. Therefore, dark points of bright points will be generated on the image of the two dimensional image sensor 42 corresponding to the defective granules and foreign matter under such condition.

Further, the presence of dark points or bright points in the image is detected by the image processor 46, and if any dark points or bright points are detected, the selector 36 is caused to actuate for a prescribed period of time by the selector controlling means (47, 48) so as to remove granules 3 in the area where defective granules or foreign matter are contained.

Figure 15:
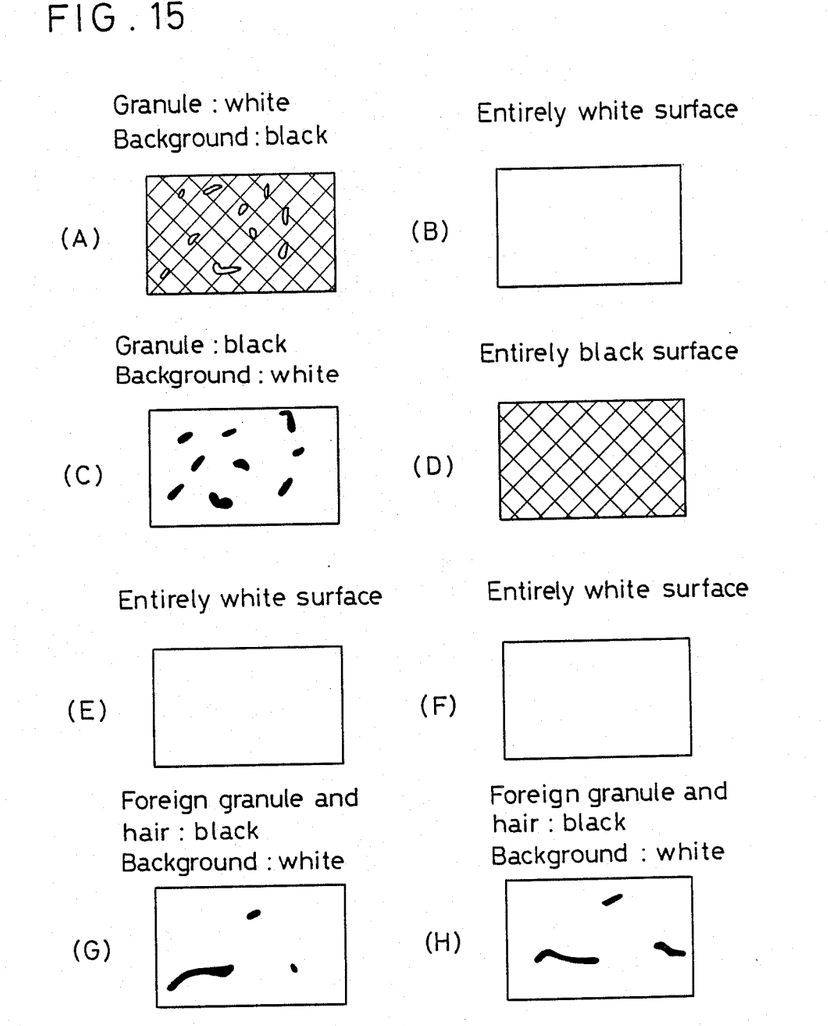

FIG. 15 (A) through (H) represent the status of the transmission light source 45 and reflection light source 44 and the status of the image according to the quantity of granules 3 and the presence of defective granules and foreign matter.

FIG. 15 (A) represents the case of the reflected light only where granules 3 are less, granules 3 are white and the background is black. FIG. 15 (B) represents the case of the reflected light only where granules 3 are very much (the surface entirely is covered with granules), and the entire surface becomes white. FIG. 15 (C) represents the case of the transmitted light only where granules 3 are less, granules 3 are black and the background white. FIG. 15 (D) represents the case of the transmitted light only where granules 3 are very much and the entire surface becomes black.

FIG. 15 (E) represents the case where the reflected light and the transmitted light are balanced and granules 3 are less and denotes the case of only non-defectives where the entire surface becomes white. FIG. 15 (F) represents the case where the reflected light and the transmitted light are balanced and granules 3 are very much and denotes the case of only non-defectives where the entire surface becomes white. FIG. 15 (G) represents the case where the reflected light and the transmitted light are balanced and granules 3 are less and denotes the case where hair and foreign granules etc. are present. Under such conditions, hair and foreign granules become dark points while the background becomes white. FIG. 15 (H) represents the case where the reflected light and the transmitted light are balanced and granules 3 are very much and denotes the case where hair and foreign granules are present. Under such conditions, hair and foreign granules become dark points and the background becomes white.

The image processor 46 which generates defective warning signals based on the image of the two dimensional image sensor and the selector controlling means (delay circuit 47 and retriggerable one-shot multiple vibrator 48) according to this embodiment of the present invention are the same as the aforementioned embodiment. Therefore, description thereof is omitted.

The image pickup period is determined by the falling speed of granules in the inspection visual field P'.

Figure 16:
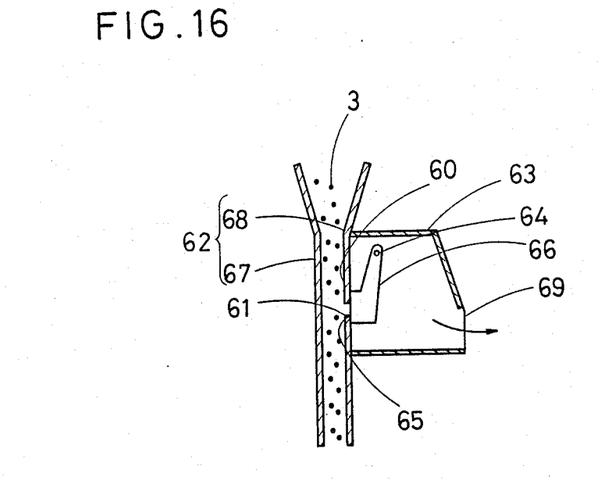
FIG. 16 is a cross sectional view showing the closed shutter of the selector according to the present invention.
Figure 17:
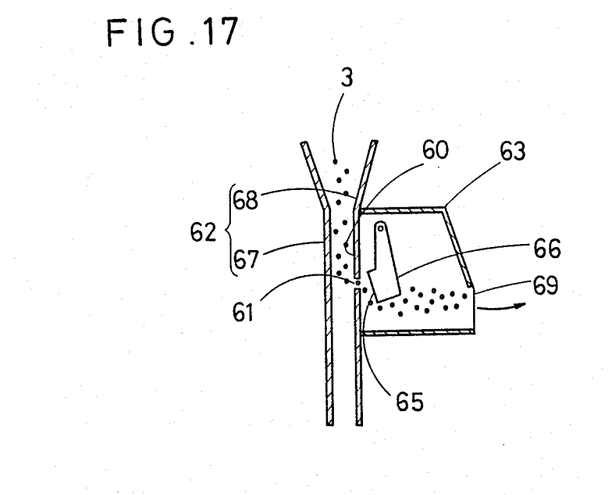
FIG. 17 is a cross sectional view showing the opened shutter of the selector according to the present invention.
Figure 18:
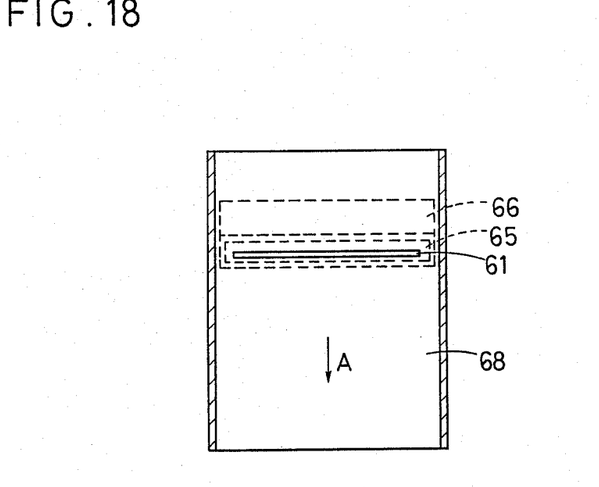
FIG. 18 is a partially sectional view showing the suction slit as viewed from inside the passage.
Figure 19:
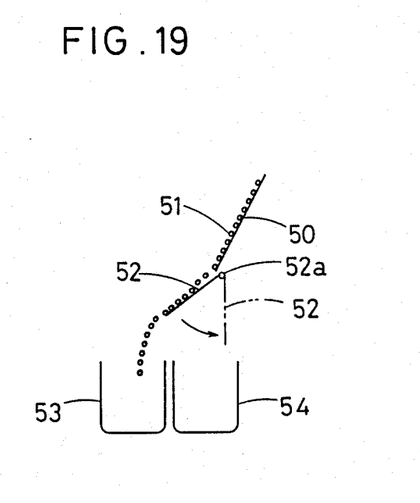
FIGS. 19 and 20 are descriptive diagrams of other selectors.

The selector will now be described. FIG. 16 through FIG. 18 show preferred embodiment of the selector according to the present invention, which comprises a passage 62 causing granules 3 to flow downward and having a suction slit 61 for sucking granules 3 over the wall surface 60; a suction chamber 63 formed on the outside of this passage 62, enveloping the suction slit 61, so as to suck by the air granules 3 flowing down the passage 62; a shutter 66 having a base end oscillatably supported by the shaft supporting section 64 in the suction chamber 63 and at its top a opening section 65 for opening and closing the suction slit 61 by means of oscillating operation.

The aforementioned passage 62 is formed by combining two falling guide plates 67, 68 so as to cause the granules 3 to flow downward in layer through the passage 62.

The aforementioned suction slit 61 is formed on one falling guide plate 68 and has prescribed width and length according to the falling width of granules 3 as shown in FIG. 18, so that the longitudinal direction is arranged at right angle to the granule falling direction of the arrow A.

It is preferred to provide the width of the suction slit 61 to be minimum to allow suction of granules 3 because defective granules 3 are discharged in minute quantity.

The aforementioned suction chamber 63 has an opening 69 and by sucking the air from the opening 69 using a pump which is not shown in drawings, the inside of the suction chamber 63 is held at low pressure with the shutter 66 being closed, so that defective granules 3 are recovered from the opening 69 when the shutter 66 is opened.

The aforementioned shutter 66 is oscillatably supported by the shaft supporting section 64, and it is preferred that the shutter 66 is driven to operate at high speed.

The suction slit 61 of this selector is closed normally by the shutter 66 and granules 3 are not sucked in by the suction slit 61. Granules 3 is fall down through the passage 62 to be recovered into a non-defective granule container.

If defective granules 3 are detected in granules 3, when the defective granules 3 have reached the front of the suction slit 61, the shutter 66 is oscillated to open the suction slit 61, the air is sucked into the suction chamber 63 whose pressure is low, from the passage 62, defective granules 3 are sucked into the suction chamber 63 through the suction slit 61, thereby removing defective granules 3 from the passage 62.

According to this embodiment, in order to suck defective granules 3 through the suction slit 61, there is no possibility to suspend or disturb conveyance of granules 3 which are not defective while the defective granules 3 can be discharged in minute quantity and the defective granules 3 can be recovered completely. In addition, because the suction slit 61 is relatively narrow and the air flowing through the suction slit 61 becomes high speed, there is no possibility for the suction slit 61 to be clogged by the bridge of the defective granules 3.

Also, because the suction slit 61 is opened and closed by oscillation of the shutter 66 in the suction chamber 63 and because there is no possibility for granules 3 to attach to the shaft supporting section 64 of the shutter 66, there occurs no faulty operation of the shutter 66.

Selectors of other examples are shown in FIG. 19 through FIG. 22. The selector shown in FIG. 19 causes granules 51 to fall down along the passage 50, when defective granules 51 reach the separator 52, the separator 52 is changed over from the status of the actual line to the status of imaginary line, thereby causing defective granules 51 to fall into the defective container 54 without causing the defective granules 51 to fall into the non-defective container 53.

Figure 20:
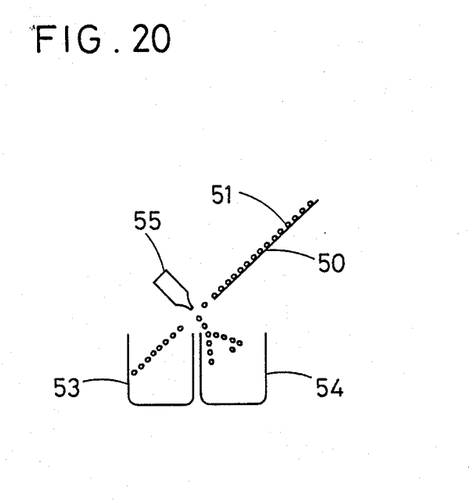

The selector shown in FIG. 20 causes granules 51 to fall down along the passage 50, blows off the jet air instantaneously from the air gun 55 when the defective granules 51 reached the front of the air gun 55, and causes defective granules 51 to fall into the defective container 54.

Figure 21:
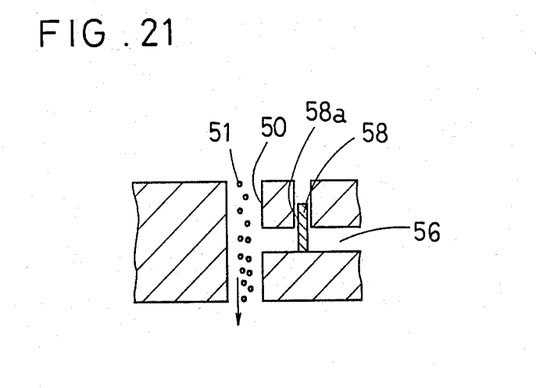
FIGS. 21 and 22 are descriptive diagrams of further selectors.
Figure 22:
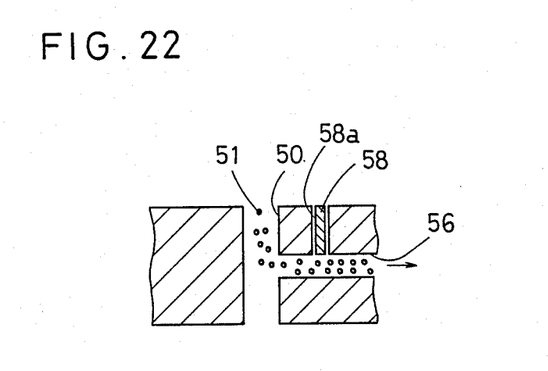

The selectors shown in FIG. 21 and FIG. 22 form the suction passage 56 which crosses with the passage 50 in the form of the letter T, and are provided with the shutter 58 which slides to open and close the suction passage 56.

Normally, the shutter 58 is closed as shown in FIG. 21 and the sucking motion is not performed, but when defective granules 51 has reached the front of the suction passage 56, the shutter 58 is slid as shown in FIG. 22 to open the suction passage 56, and remove defective granules 51 from the passage 50 by sucking defective granules 51 using air.

What is claimed is:

1. A granule inspection apparatus comprising a pair of transparent rotating bodies which each rotate about a center axis thereof, said rotating bodies being positioned to present mutually opposed rotating surfaces therebetween to define a granule falling passage; a granule conveying and sheet forming means with an opening above said granule falling passage; a selector installed under said granule falling passage to remove granules; cleaner means for cleaning the surfaces of said pair of transparent rotating bodies at positions other than at said granule falling passage; a light source for reflected light at the side of one transparent rotating body for lighting granules that have fallen through said granule falling passage, a light source for transmitted light at the side of the other transparent rotating body for transmission of light through the granules that have fallen through said granule falling passage, means for sensing and comparing the light transmitted through the granules and the light reflected from the granules comprising an image sensor for picking up images of granules falling through said granule falling passage; and image processing means for processing image signals of said image sensor to detect the presence of defective granules and foreign matter in said granules falling down through said granule falling passage and means for issuing defective warning signals; a selector controlling means for operating said selector for a prescribed period of time in response to defective warning signal from said image processing means to remove defective granules and foreign matter; the quantity of the light of said light source for reflected light from non-defective granules and the quantity of the light of said light source for transmitted light being equally set.

2. The apparatus according to claim 1, wherein said transparent rotating bodies are transparent rotating cylinders.

3. The apparatus according to claim 2, wherein the center axes of said pair of transparent rotating cylinders are parallel.

4. The apparatus according to claim 3, wherein the center axes of said transparent rotating cylinders are horizontal.

5. The apparatus according to claim 4, wherein both said transparent rotating cylinders have an outer surface and rotate in a direction so that said outer surface of each rotating cylinder moves downward at an opposing portion thereof.

6. The apparatus according to claim 2, wherein said pair of transparent rotating cylinders accommodates therein said light source for reflection and light source for transmission respectively.

7. The apparatus according to claim 1, wherein said transparent rotating bodies are overlapping transparent rotating disks having center axes that are spaced apart.

8. The apparatus according to claim 7, wherein said transparent rotating disks rotate in a direction to move downward at said overlapping portion thereof.

9. The apparatus according to claim 7, wherein at least one of said transparent rotating disks contacts said cleaner at a non-overlapping portion thereof.

10. The apparatus according to claim 1, wherein said selector comprises a passage causing granules to flow down and having a suction slit to suck said granules over a wall surface thereof, a suction chamber formed on the outside of this passage so as to envelop said suction slit therein and suck granules flowing down said passage by means of air, and a shutter having a base end oscillatably supported in said suction chamber and an opening and closing section for said suction slit.

11. The apparatus according to claim 1, wherein said granules are powder.

* * * * *